(12) United States Patent
Guala

(10) Patent No.: US 9,125,980 B2
(45) Date of Patent: Sep. 8, 2015

(54) DEVICE FOR MIXING MEDICAL FLUIDS AND RELATED ASSEMBLING METHOD

(75) Inventor: Gianni Guala, Turin (IT)

(73) Assignee: INDUSTRIE BORLA S.P.A., Moncalieri (Torino) (IT)

(*) Notice: Subject to any disclaimer, the term of this patent is extended or adjusted under 35 U.S.C. 154(b) by 1021 days.

(21) Appl. No.: 13/240,734

(22) Filed: Sep. 22, 2011

(65) Prior Publication Data

US 2012/0130337 A1    May 24, 2012

(30) Foreign Application Priority Data

Nov. 19, 2010 (IT) .............................. TO2010A0919

(51) Int. Cl.
| | | |
|---|---|---|
| A61M 39/00 | (2006.01) | |
| A61M 5/14 | (2006.01) | |
| A61M 5/162 | (2006.01) | |
| A61M 39/10 | (2006.01) | |
| A61M 39/02 | (2006.01) | |

(52) U.S. Cl.
CPC ............. A61M 5/1408 (2013.01); A61M 5/162 (2013.01); A61M 39/1011 (2013.01); A61M 39/02 (2013.01); A61M 2202/049 (2013.01); Y10T 29/49826 (2015.01)

(58) Field of Classification Search
USPC ................................................ 604/411, 414
See application file for complete search history.

(56) References Cited

U.S. PATENT DOCUMENTS

| | | | | |
|---|---|---|---|---|
| 4,022,205 A * | 5/1977 | Tenczar ......................... | 604/411 |
| 4,161,949 A * | 7/1979 | Thanawalla ................... | 604/411 |
| 4,187,846 A * | 2/1980 | Lolachi et al. ................ | 604/411 |
| 4,265,280 A * | 5/1981 | Ammann et al. ............... | 141/98 |
| 4,735,608 A * | 4/1988 | Sardam .......................... | 604/89 |
| 4,895,570 A * | 1/1990 | Larkin ........................... | 604/411 |
| 5,137,524 A * | 8/1992 | Lynn et al. .................... | 604/533 |
| 5,199,947 A * | 4/1993 | Lopez et al. ................... | 604/518 |
| 5,501,676 A * | 3/1996 | Niedospial et al. ........... | 604/534 |
| 5,772,261 A * | 6/1998 | Magram ........................ | 285/256 |
| 5,890,610 A * | 4/1999 | Jansen et al. .................. | 215/253 |
| 6,061,912 A * | 5/2000 | Gazaway ....................... | 30/140 |
| 7,137,974 B2 * | 11/2006 | Almasian et al. ............. | 604/411 |
| 7,297,140 B2 * | 11/2007 | Orlu et al. ..................... | 604/411 |
| 2002/0087141 A1 * | 7/2002 | Zinger et al. .................. | 604/414 |

(Continued)

FOREIGN PATENT DOCUMENTS

| | | |
|---|---|---|
| DE | 101 50 994 A1 | 4/2003 |
| EP | 1 492 590 B1 | 7/2007 |
| WO | WO 03/086529 A1 | 10/2003 |

OTHER PUBLICATIONS

Italian Search Report, completed on Oct. 24, 2011, for corresponding Italian Patent Application No. TO 2010A000919 filed on Nov. 19, 2010.

*Primary Examiner* — Melanie Hand
*Assistant Examiner* — Paula L Craig
(74) *Attorney, Agent, or Firm* — Heslin Rothenberg Farley & Mesiti P.C.; Victor A. Cardona, Esq.

(57) ABSTRACT

A medical device, particularly for mixing medical fluids, includes two tubular bodies made of materials of different elasticity having respective open ends to be joined together. The end of the second body is inserted axially by friction within the end of the first body and is then blocked via radial projections, which are obtained by plastic deformation of the wall of the end of the first body and are engaged against the end of the second body.

4 Claims, 4 Drawing Sheets

(56) References Cited

U.S. PATENT DOCUMENTS

| | | | |
|---|---|---|---|
| 2003/0191445 A1* | 10/2003 | Wallen et al. | 604/411 |
| 2005/0033260 A1* | 2/2005 | Kubo et al. | 604/411 |
| 2007/0088315 A1* | 4/2007 | Haindl | 604/411 |
| 2008/0077176 A1* | 3/2008 | Hanlon et al. | 606/201 |

* cited by examiner

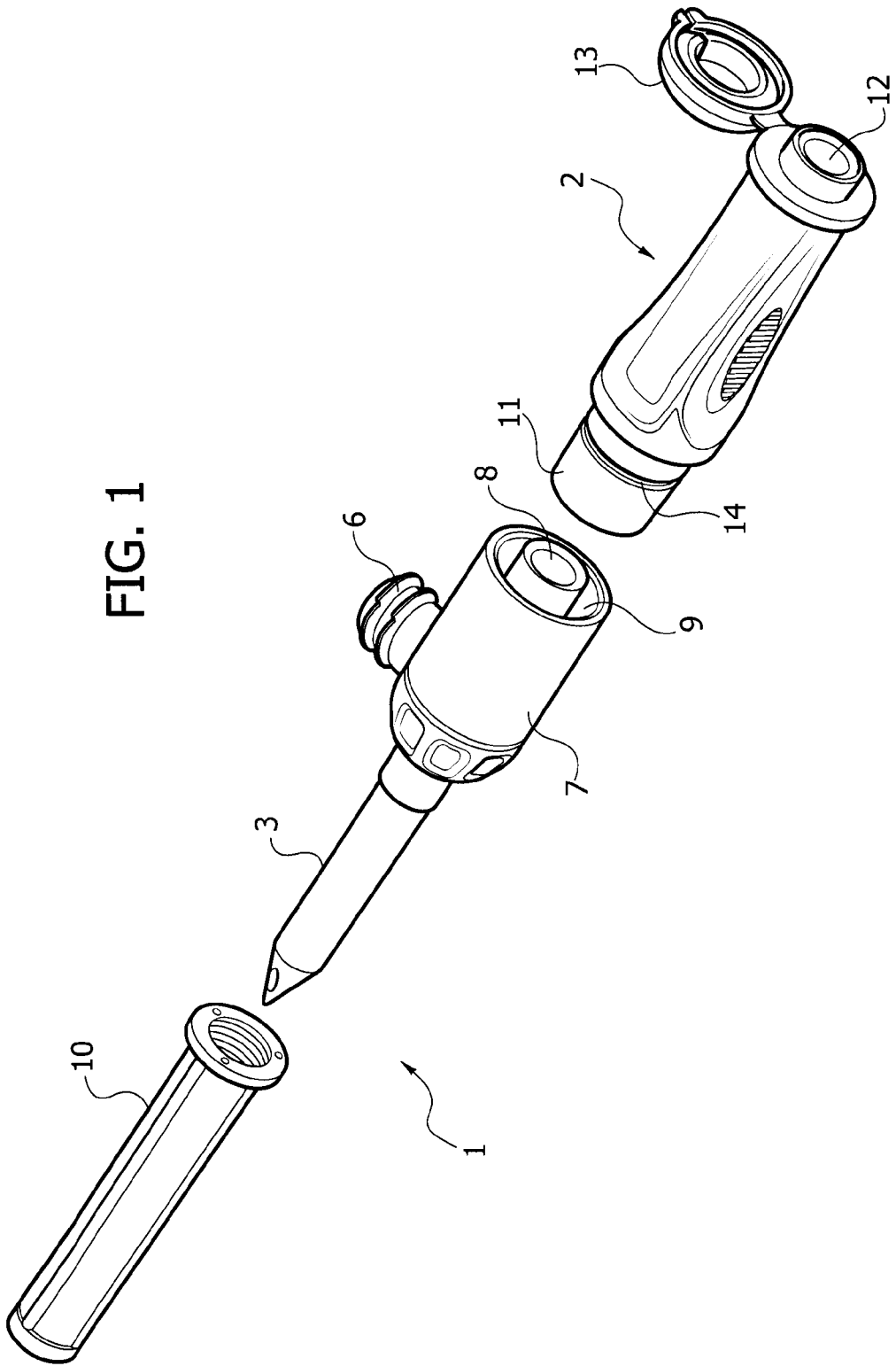

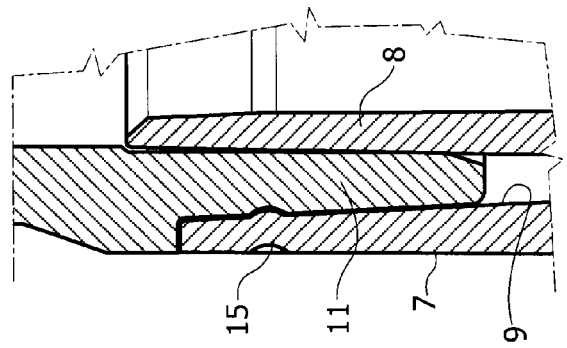
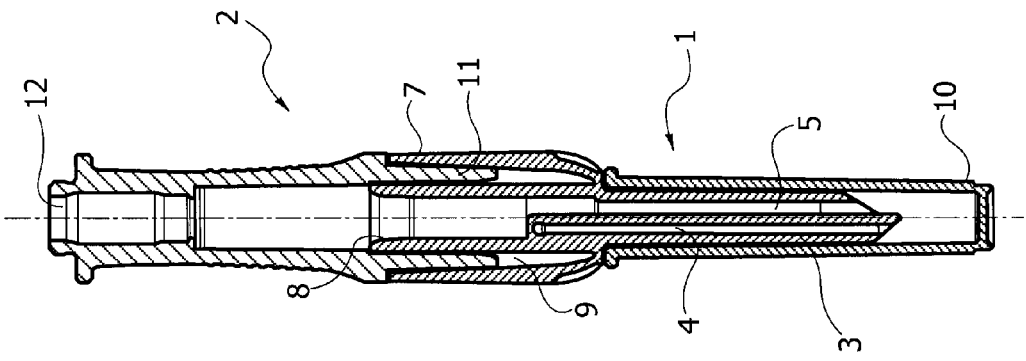
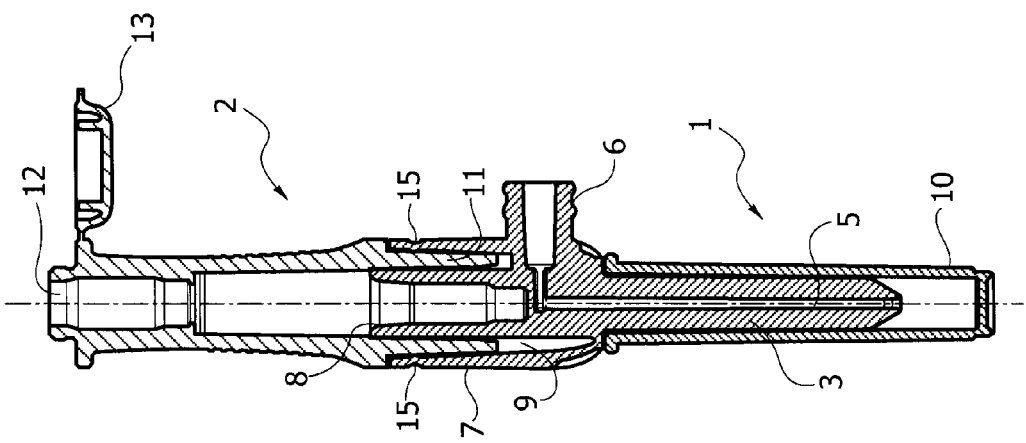

DEVICE FOR MIXING MEDICAL FLUIDS AND RELATED ASSEMBLING METHOD

CROSS REFERENCE TO RELATED APPLICATIONS

This application claims priority from Italian patent application No. TO2010A000919, filed on Nov. 19, 2010, the entire disclosure of which is incorporated herein by reference.

FIELD OF THE INVENTION

The present invention relates in general to medical devices and more in particular to a device for mixing medical fluids including two distinct and coaxial tubular bodies of which a first body, made of a first material, has a hollow spike, which can be inserted into a container for a medical fluid, and a second body, made of a second material more elastic than the first material, has an outlet set on the side opposite to the spike. The first body moreover has a lateral access for introduction of a second medical fluid that can be mixed with the first.

The two bodies have respective open ends of mutual joining, of which the end of the second body is inserted axially and blocked within the end of the first body.

Mixing devices of the above sort are typically used for extraction of a toxic drug contained within the container, in which the hollow spike is inserted for mixing of said drub with a secondary fluid and then for drawing in the mixture thus obtained through the outlet.

PRIOR ART

In the above known mixing devices there is the problem of providing a secure permanent connection between the two tubular bodies, which, as has been said, are made of two different materials, traditionally plastic materials: the first body may be made of a thermoplastic polymeric material (for example, polypropylene, polycarbonate, ABS, and the like), and the second body may be made of an elastomeric polymeric material or thermoplastic rubber. The irreversible connection between such materials, which is necessary for preventing in use any risk of accidental leakage of medical fluids, cannot be obtained in a sufficiently safe and reliable way via glues or adhesives.

In an attempt to solve said problem, it has been proposed in the patent No. EP-1492590 B1, filed in the name of Carmel Pharma AB, to make the connection between the two bodies of the mixing device by means of insertion by friction of the open end of the second body within the open end of the first body and via a snap-action connection: the open end of the second body is formed with one or more radial projections designed to engage one or more respective openings formed in the wall of the end of the first body.

This arrangement, albeit suitable for rendering irreversible the connection between the two bodies, hence preventing any risk of accidental separation, does not exclude the risk of leakage of medical fluid through the areas of mutual snap-action coupling between the ends of the two bodies, which constitutes a serious drawback.

SUMMARY OF THE INVENTION

The object of the present invention is to overcome the aforesaid drawback and hence to provide a device for mixing medical fluids and a method for its assembly in which the irreversible connection between the two bodies of the device is free from by any risk of accidental leakage of medical fluid outside.

According to the invention, the above object is achieved thanks to the fact that the connection between the aforesaid open ends of the first and second bodies of the device is obtained via radial projections engaged against the end of the second body and obtained by plastic deformation of the wall of said end of the first body following upon axial insertion by friction of the end of the second body into the end of the first body.

Thanks to this arrangement, which eliminates the aforesaid known formations for mutual snap-action engagement between the two bodies of the device, any risk of leakage of medical fluids during use is eliminated.

The radial projections of the wall of the end of the first body, obtained via a purposely provided apparatus for plastic deformation by means of an apparatus with mobile punches that act radially, conveniently have substantially spherical surfaces.

BRIEF DESCRIPTION OF THE DRAWINGS

The invention will now be described in detail with reference to the annexed drawings, which are provided purely by way of non-limiting example and in which:

FIG. 1 is an exploded perspective view of a device for mixing medical fluids according to the invention represented prior to its assembly;

FIG. 6 is an axial cross-sectional view of the assembled device;

FIG. 7 is an axial cross-sectional view similar to that of FIG. 6 but rotated through 90°; and FIG. 8 shows a detail of FIG. 6 at a larger scale.

DETAILED DESCRIPTION OF THE INVENTION

Figure 4:
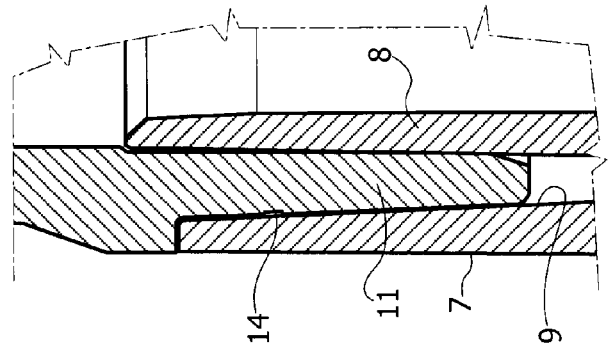
FIG. 4 shows a detail of FIG. 2 at a larger scale.

With initial reference to FIG. 1, a device for mixing medical fluids according to the invention comprises a first hollow body 1 and a second hollow body 2 obtained as distinct elements by means of moulding of two different plastic materials, of which the material of the second body 2 is more elastic than the material of the first body 1. By way of example, the first body 1 can be made of a thermoplastic polymeric material such as polypropylene, polycarbonate, or ABS, whilst the material of the second body 2 can be an elastomeric polymer or a thermoplastic rubber. Said materials are purely indicative and non-limiting.

The first body 1 has at one end a hollow spike 3, which is to be inserted in a container for a first medical fluid having a first axial inlet passage 4 for the first fluid, a second axial passage 5 connected with a lateral tubular connector 6 for injection of a second medical fluid, and an open end 7 opposite to the spike 3. Extending within the open end 7 is an integral tubular appendage 8 in communication with the axial passage 4, which defines with said end 7 an annular seat 9.

Designated by 10 is a protective cap that can be fitted axially in an extractable way on the spike 3.

The second body 2 has an open end 11 for connection to the first body 1, with the modalities clarified in what follows, and at the opposite end an outlet opening 12 that is normally closed via an openable integral plug 13.

On the end 11 of the body 2 there can be provided an annular groove 14, the presence of which is not, however, indispensable.

Figure 3:
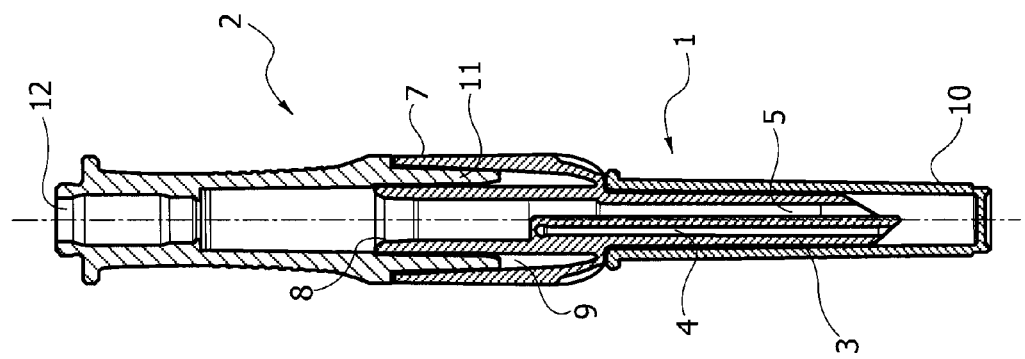
FIG. 3 is an axial cross-sectional view similar to that of FIG. 2 but rotated through 90°.
Figure 2:
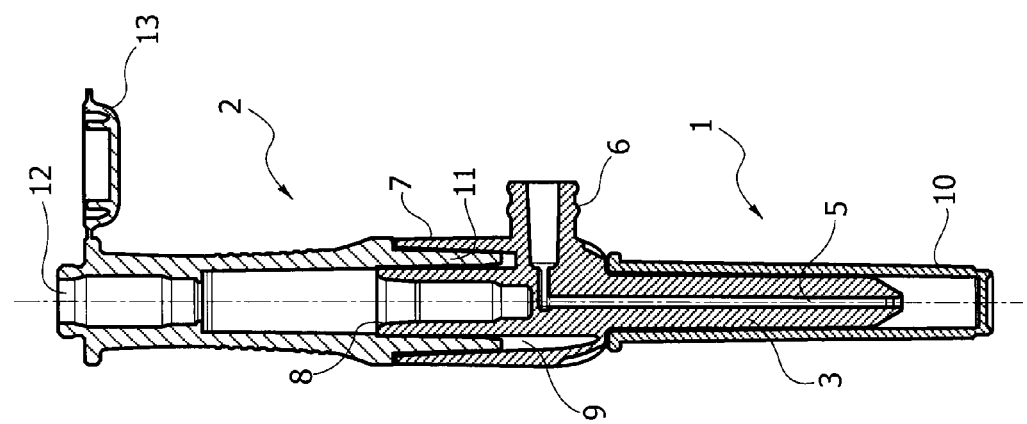
FIG. 2 is an axial cross-sectional view of the mixing device represented following upon a first assembly step.
Figure 5:
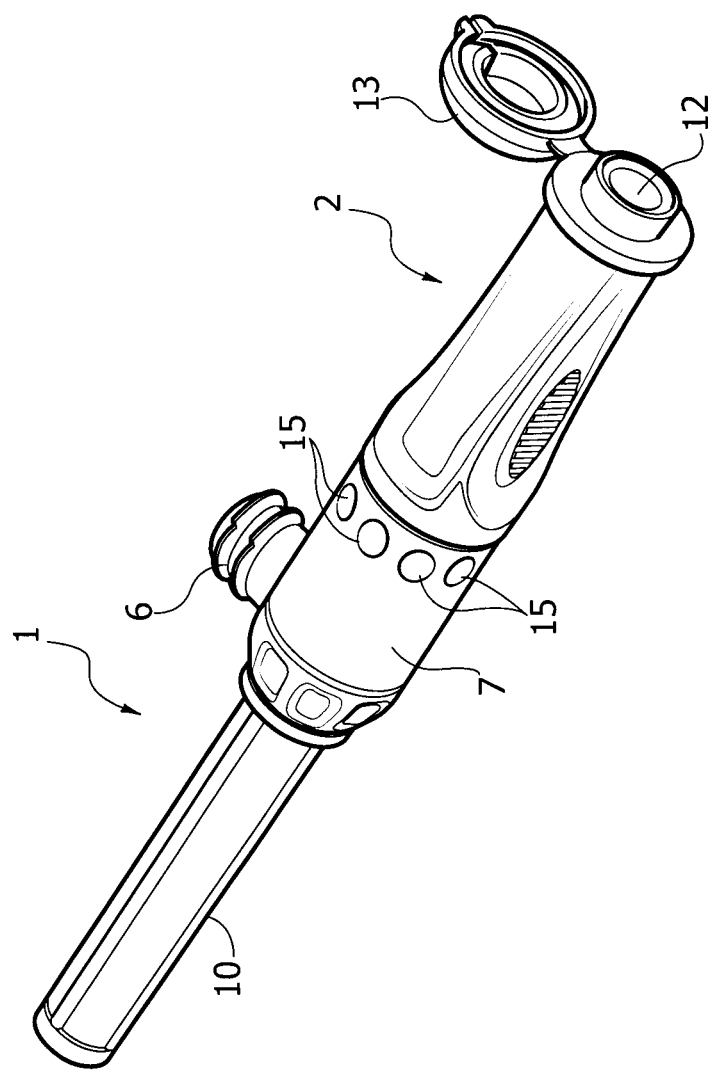
FIG. 5 is a perspective view that shows the mixing device in its final configuration, following upon a second assembly step.

FIGS. 2 and 3 illustrate the mixing device following upon a first assembly step between the body 1 and the body 2. Said step envisages axial introduction of the end 11 of the body 2 right home within the annular seat 9. The dimensions of the outer and inner surfaces of the end 11 are such as to provide a forced fit by friction, respectively, with the inner surface of the end 7 and with the outer surface of the tubular appendage 8, in the way represented in greater detail in FIG. 4. Notwithstanding said axial fit by friction, the union between the bodies 1 and 2 would not be sufficient to prevent a possible even just partial axial separation thereof, with the consequent unacceptable risk, in use, of accidental leakage of the medical fluids mixed within the body 1. For said reason, the assembly between the bodies 1 and 2 envisages, according to the invention, the further step represented in FIGS. 5 to 8, following upon which the bodies 1 and 2 are joined together in a permanent and substantially irreversible way.

Said step envisages, according to the invention, formation of one or more radial projections 15 on the wall of the end 7 of the body 1, which are preferably arranged in a ring and are obtained by plastic deformation so as to project against the outer surface of the end 11 of the body 2, engaging against it in the way represented in greater detail in FIG. 8. Said radial projections 15, corresponding to the annular groove 14 of the end 11 of the body 2, where envisaged, may be obtained by applying localized compression on the wall of the end 7 of the body 1 with the aid of an apparatus, not illustrated, comprising a ring of radial punches that can be displaced, with respect to a seat for insertion of the device, between a retracted position and an advanced position in which they deform radially the wall of the end 7 by the amount sufficient to provide the projections 15. In this way, produced in the wall of the end 7 are displacements of material that generate on its outer surface concave impressions, corresponding to which on its outer surface are convex projections that constitute the projections 15.

Engagement of the projections 15 against the surface of the end 11 of the body 2 thus provides permanent and irreversible mutual mechanical blocking between the bodies 1 and 2, already joined by axial forcing in the way clarified previously, thus preventing in a safe and reliable way any risk of an accidental separation thereof. Said irreversible union, obtained without the need to make holes or openings in the areas of union between the bodies 1 and 2, prevents in an equally safe way the risk of accidental leakage of medical fluids during use of the mixing device.

Of course, the details of construction and the embodiments may vary widely with respect to what has been described and illustrated herein, without thereby departing from the scope of the present invention, as defined in the ensuing claims.

What is claimed is:

1. A medical device for mixing medical fluids, comprising:
   two distinct and coaxial tubular bodies, of which a first body is made of a first plastic material and is formed with a hollow spike insertable in a container for medical fluid,
   a second body made of a second plastic material more elastic than the first material and has an outlet set on a side opposite to said spike,
   wherein said two bodies have respective open ends to be joined together, of which a second open end of the second body is inserted axially by friction within a first open end of the first body and blocked via a substantially irreversible connection,
   said first body comprising radial projections on a first wall of said first end of said first body, said projections arranged in a ring and having substantially spherical surfaces;
   said radial projections engaged against said second end of the second body and formed by plastic deformation of said first wall after said second end of the second body is inserted within said first end of the first body such that said projections project against an outer surface of said second end of said second body to connect said first end to said second end to cause said substantially irreversible connection.

2. The device according to claim 1, wherein said second open end of the second body is inserted axially between said first open end of the first body and a coaxial tubular appendage defining with first said open end of the first body an annular gap.

3. The device according to claim 1, wherein said hollow spike has a first axial inlet passage for said medical fluid and a second axial passage connected to a lateral access for introduction of a second medical fluid.

4. The device according to claim 1, wherein said second open end of the second body has an annular groove axially corresponding to said at least one radial projection of said first open end of the first body.

* * * * *